(12) United States Patent
Reubinoff et al.

(10) Patent No.: US 11,230,696 B2
(45) Date of Patent: Jan. 25, 2022

(54) LARGE SCALE PRODUCTION OF RETINAL PIGMENT EPITHELIAL CELLS

(71) Applicant: Hadasit Medical Research Services and Development Ltd., Jerusalem (IL)

(72) Inventors: Benjamin Eithan Reubinoff, Doar-Na HaEla (IL); Orna Singer, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 15/748,541

(22) PCT Filed: Jul. 28, 2016

(86) PCT No.: PCT/IL2016/050829
§ 371 (c)(1),
(2) Date: Jan. 29, 2018

(87) PCT Pub. No.: WO2017/017686
PCT Pub. Date: Feb. 2, 2017

(65) Prior Publication Data
US 2018/0216064 A1 Aug. 2, 2018

Related U.S. Application Data

(60) Provisional application No. 62/198,160, filed on Jul. 29, 2015.

(51) Int. Cl.
*C12N 5/079* (2010.01)
*A61P 27/02* (2006.01)
*A61K 9/00* (2006.01)
*A61K 35/30* (2015.01)

(52) U.S. Cl.
CPC .......... *C12N 5/0621* (2013.01); *A61K 9/0051* (2013.01); *A61K 35/30* (2013.01); *A61P 27/02* (2018.01); *C12N 2500/38* (2013.01); *C12N 2501/115* (2013.01); *C12N 2501/15* (2013.01); *C12N 2502/13* (2013.01); *C12N 2506/02* (2013.01); *C12N 2533/52* (2013.01); *C12N 2533/54* (2013.01)

(58) Field of Classification Search
CPC .......... C12N 2501/15; C12N 5/0621
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | Mcconnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,755,785 A | 5/1998 | Rowsey et al. |
| 5,843,780 A | 12/1998 | Thomson |
| 5,941,250 A | 8/1999 | Aramant et al. |
| 5,962,027 A | 10/1999 | Hughes |
| 6,045,791 A | 4/2000 | Liu |
| 6,090,622 A | 7/2000 | Gearhart et al. |
| 2004/0067580 A1 | 4/2004 | Amit et al. |
| 2007/0212777 A1 | 9/2007 | Reubinoff |
| 2011/0027333 A1 | 2/2011 | Idelson et al. |
| 2011/0039338 A1 | 2/2011 | Yoshida et al. |

(Continued)

FOREIGN PATENT DOCUMENTS

| | | |
|---|---|---|
| CN | 101688178 A | 3/2010 |
| CN | 101848994 A | 9/2010 |
| EP | 2128244 A1 | 12/2009 |

(Continued)

OTHER PUBLICATIONS

Liu et al. "Chemical Modulation of Cell Fate in Stem Cell Therapeutics and Regenerative Medicine", Cell Chemical Biology Aug. 18, 2016, 24 pages (Year: 2016).*
Jang et al. "Modulation of Stem Cell Differentiation with Biomaterials" International Journal of Stem Cells vol. 3, No. 2, 2010, 5 pgs (Year: 2010).*
Strassburg et al. "Co-culture induces mesenchymal stem cell differentiation and modulation of the degenerate human nucleus pulposus cell phenotype" Regen. Med. (2010) 5(5), 701-711 (Year: 2010).*
Nash et al. "The Response of Cultured Human Retinal Pigment Epithelium to Hypoxia: A Comparison to Other Cell Types" Invest Ophthalmol Vis Sci. May 1994;35(6):2850-6.*
Idelson et al. "Directed Differentiation of Human Embryonic Stem Cells into Functional Retinal Pigment Epithelium Cells" Cell Stem Cell 5, 396-408, Oct. 2, 2009.*

(Continued)

*Primary Examiner* — Thane Underdahl
(74) *Attorney, Agent, or Firm* — Mintz, Levin, Cohn, Ferris, Glovsky and Popeo, P.C.

(57) ABSTRACT

A method of generating retinal pigment epithelial (RPE) cells is disclosed. The method comprises: (a) culturing human pluripotent stem cells in a human feeder cell-conditioned medium to obtain a cultured population of human pluripotent stem cells; (b) culturing said cultured population of human pluripotent stem cells in a medium comprising a differentiating agent to obtain differentiating cells; and (c) culturing said differentiating cells in a medium comprising one or more members of the TGFβ superfamily.

27 Claims, 1 Drawing Sheet

(56) References Cited

U.S. PATENT DOCUMENTS

2013/0196369 A1    8/2013    Hikita et al.

FOREIGN PATENT DOCUMENTS

| | | |
|---|---|---|
| EP | 2142641 A2 | 1/2010 |
| EP | 2147094 A1 | 1/2010 |
| EP | 2307539 A1 | 4/2011 |
| GB | 2327675 A | 2/1999 |
| JP | 2010524457 A | 7/2010 |
| JP | 2011529329 A | 12/2011 |
| JP | 2018502575 A | 2/2018 |
| KR | 1020110036523 A | 4/2011 |
| WO | 01/55114 A1 | 8/2001 |
| WO | 02/060875 A1 | 8/2002 |
| WO | 03/068233 A1 | 8/2003 |
| WO | 2005/014549 A1 | 2/2005 |
| WO | 2006/040763 A2 | 4/2006 |
| WO | 2006/070370 A2 | 7/2006 |
| WO | 2006/070370 A3 | 3/2007 |
| WO | 2008/129554 A1 | 10/2008 |
| WO | 2010/013845 A1 | 2/2010 |
| WO | 2010/140698 A1 | 12/2010 |
| WO | 2013/114360 A1 | 8/2013 |
| WO | 2013/184809 A1 | 12/2013 |
| WO | WO 2014/121077 * | 8/2014 |
| WO | 2016/108240 A1 | 7/2016 |

OTHER PUBLICATIONS

Gibco "Cell Culture Basics" available on Feb. 11, 2014 via Wayback Machine, 62 pages (Year: 2014).*
International Preliminary Report on Patentability issued in International Application No. PCT/IL16/50829, dated Feb. 8, 2018, 9 pages.
International Search Report issued in International Application No. PCT/IL16/50829, dated Oct. 12, 2016, 11 pages.
(2009) Nutristem(Tm) Serum-Free Medium For Human ES Cell Culture, CosmoBionews, 76:2 pages. (English Document Not Available).
Algvere et al. (Mar. 1997) "Transplantation of RPE in Age-related Macular Degeneration: Observations in Disciform Lesions and Dry RPE Atrophy", Graefe's Archive for Clinical and Experimental Ophthalmology, 235 (3):149-158.
Aoi et al. (Aug. 1, 2008) "Generation of Pluripotent Stem Cells from Adult Mouse Liver and Stomach Cells", Science, 321(5889):699-702.
Ausubel et al. (1989) "Preparation of a Specific Retrovirus Producer Cell Line", Current Protocols in Molecular Biology, Greene Publishing Associates, Sections 9.10-9.14, 1087-1136.
Bharti et al. (Feb. 7, 2011) "The New Paradigm: Retinal Pigment Epithelium Cells Generated From Embryonic or Induced Pluripotent Stem Cells", Pigment Cell & Melanoma Research, 24(1):21-34 (21 pages).
Bigar et al. (Aug. 1992) "Corneal Transplantation", Current Opinion in Ophthalmology, 3(4):473-481.
Birren Bruce (May 1998) "Genome Analysis Laboratory Manual Series", Cold Spring Harbor Laboratory Press, 4 pages.
Bongso et al. (Aug. 1989) "Improved Quality of Human Embryos when Co-Cultured with Human Ampullary Cells", Human Reproduction, 4(6):706-713.
Buchholz et al. (Apr. 18, 2013) "Rapid and Efficient Directed Differentiation of Human Pluripotent Stem Cells Into Retinal Pigmented Epithelium", Stem Cells Translational Medicine, 2(5):384-393.
Chacko et al. (Feb. 24, 2000) "Survival and Differentiation of Cultured Retinal Progenitors Transplanted in the Subretinal Space of the Rat", Biochemical and Biophysical Research Communications, 268(3):842-846.
Chung et al. (Feb. 7, 2008) "Human Embryonic Stem Cell Lines Generated without Embryo Destruction", Cell Stem Cell, 2(2):113-117.
Claridge et al. (1995) "Should second eye cataract surgery be rationed?", (Pt 6 Su):47-49.
Doetschman et al. (May 1988) "Establishment of Hamster Blastocyst-Derived Embryonic Stem (ES) Cells", Developmental Biology, 127(1):224-227.
Gardner et al. (Jan. 1998) "Culture and Transfer of Human Blastocysts Increases Implantation Rates and Reduces the Need for Multiple Embryo Transfers", Fertility and Sterility, 69(1):84-88.
Giles et al. (Oct. 1993) "Pluripotency of Cultured Rabbit Inner Cell Mass Cells Detected by Isozyme Analysis and Eye Pigmentation of Fetuses Following Injection into Blastocysts or Morulae", Molecular Reproduction and Development, 36(2):130-138.
Graves et al. (Dec. 1993) "Derivation and Characterization of Putative Pluripotential Embryonic Stem Cells from Preimplantation Rabbit Embryos", Molecular Reproduction and Development, 36(4):424-433.
Iannaccone et al. (May 1994) "Pluripotent Embryonic Stem Cells from the Rat Are Capable of Producing Chimeras", Developmental Biology, 163(1):288-292.
Lane et al. (Oct. 1, 2014) "Engineering Efficient Retinal Pigment Epithelium Differentiation From Human Pluripotent Stem Cells", Stem Cells Translational Medicine, 3(11):1295-1304.
Mills et al. (Jul. 2001) "From mouse to man: generating megabase chromosome rearrangements", 17(6):331-339.
Mitalipova et al. (2001) "Pluripotency of Bovine Embryonic Cell Line Derived from Precompacting Embryos", Cloning, 3(2):59-67.
Notarianni et al. (1991) "Derivation of Pluripotent, Embryonic Cell Lines from the Pig and Sheep", Journal of Reproduction and Fertility Supplement, 43:255-260.
Oplinger et al. (Apr. 1998) "A Comparison of Corneal Autografts With Homografts", Ophthalmic Surgery, Lasers and Imaging Retina, 29(4):305-308.
Park et al. (Jan. 10, 2008) "Reprogramming of Human Somatic Cells to Pluripotency With Defined Factors", Nature, 451(7175):141-146.
Patel et al. (Apr. 2000) "Indications for and Outcomes of Repeat Penetrating Keratoplasty, 1989-1995", Ophthalmology, 107(4):719-724.
Peyman et al. (Feb. 1991) "A Technique for Retinal Pigment Epithelium Transplantation for Age-related Macular Degeneration Secondary to Extensive Subfoveal Scarring", Ophthalmic Surgery, Lasers and Imaging Retina, 22(2):102-108 (9 pages).
Reubinoff et al. (Apr. 18, 2000) "Embryonic stem cell lines from human blastocysts: somatic differentiation in vitro", Nature Biotechnology, 18(4): 399-404.
Richards et al. (Sep. 2002) "Human Feeders Support Prolonged Undifferentiated Growth of Human Inner Cell Masses and Embryonic Stem Cells", Nature Biotechnology, 20(9):933-936.
Shamblott et al. (Nov. 1998) "Derivation of Pluripotent Stem Cells from Cultured Human Primordial Germ Cells", Proceedings of the National Academy of Sciences of the United States of America, 95(23):13726-13731.
Sieving et al. (Mar. 7, 2006) "Ciliary Neurotrophic Factor (CNTF) for human retinal degeneration: Phase I Trial of CNTF Delivered by Encapsulated Cell Intraocular Implants", Proceedings of the National Academy of Sciences of the United States of America, 103(10):3896-3901.
Takahashi et al. (Nov. 30, 2007) "Induction of Pluripotent Stem Cells From Adult Human Fibroblasts by Defined Factors", Cell, 131(5):861-872.
Thomson et al. (Nov. 6, 1998) "Embryonic Stem Cell Lines Derived from Human Blastocysts", Science, 282(5391):1145-1147.
Thomson et al. (Aug. 1995) "Isolation of a Primate Embryonic Stem Cell Line", Proceedings of the National Academy of Sciences of the United States of America, 92(17):7844-7848.
Thomson et al. (Aug. 1996) "Pluripotent Cell Lines Derived from Common Marmoset (*Callithrix jacchus*) Blastocysts", Biology of Reproduction, 55(2):254-259.
Thomson et al. (1998) "Primate Embryonic Stem Cells", Current Topics in Developmental Biology, 38:133-165.
Tsubota Kazuo (Nov.-Dec. 1999) "Ocular Surface Management in Corneal Transplantation, A Review", Japanese Journal of Ophthalmology, 43(6):502-508.

(56) References Cited

OTHER PUBLICATIONS

Yamanaka Shinya (Jun. 7, 2007) "Strategies And New Developments In The Generation Of Patient-Specific Pluripotent Stem Cells", Cell Stem Cell, 1(1):39-49.

* cited by examiner

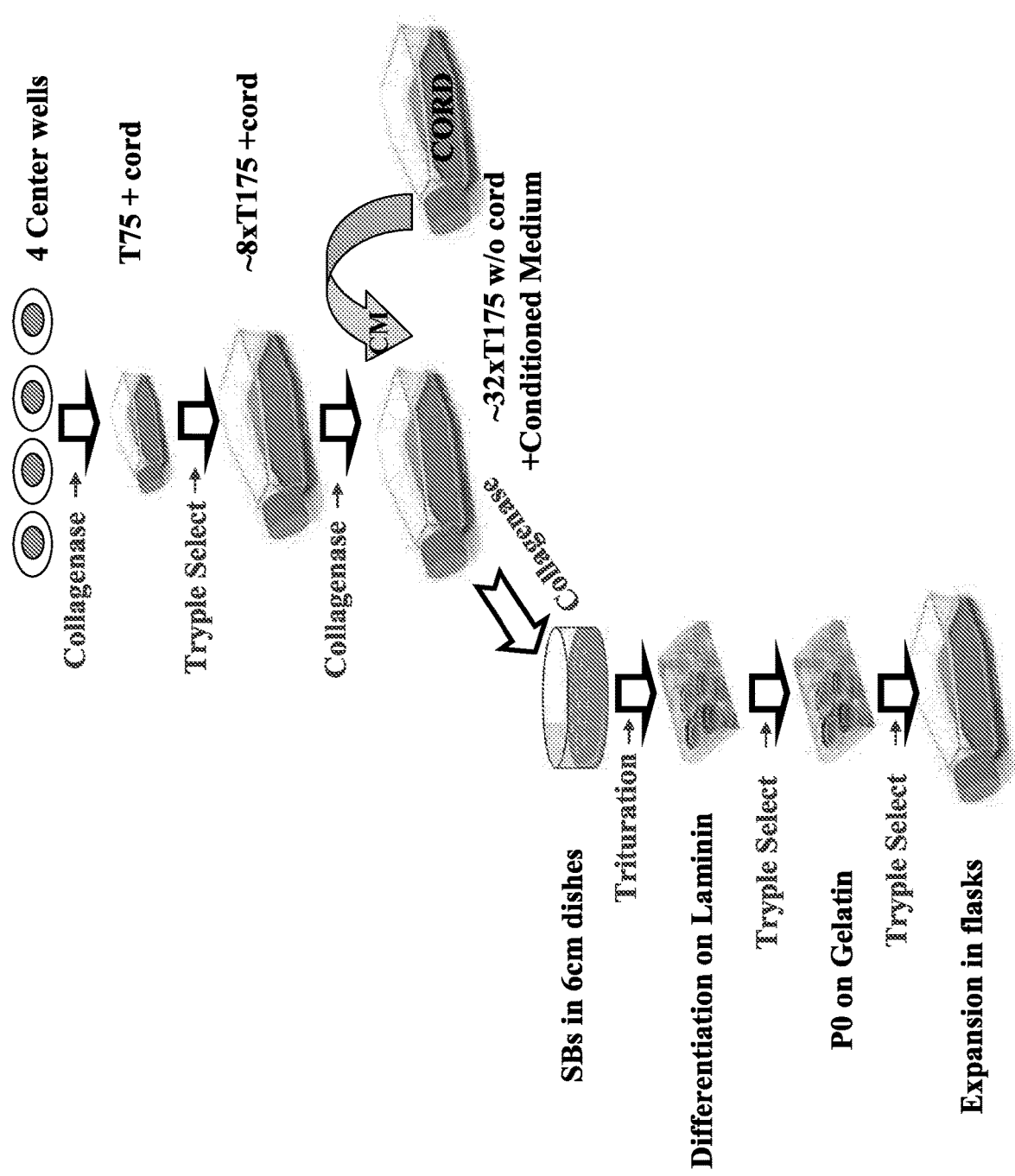

LARGE SCALE PRODUCTION OF RETINAL PIGMENT EPITHELIAL CELLS

CROSS-REFERENCE TO RELATED APPLICATIONS

This application is a National Phase Application of PCT/IL2016/050829, filed Jul. 28, 2016, which claims benefit under 35 U.S.C. § 119(e) to U.S. Provisional Application No. 62/198,160, filed Jul. 29, 2015, which is incorporated herein by reference in its entirety.

FIELD AND BACKGROUND OF THE INVENTION

The present invention, in some embodiments thereof, relates to large scale production of retinal pigment epithelial cells from embryonic stem cells.

The present invention, in some embodiments thereof, relates to retinal pigment epithelium cells and, more particularly, but not exclusively, to assessment of such cells as a therapeutic. The present invention also relates to generation of retinal pigment epithelium cells from embryonic stem cells.

The retinal pigmented epithelium (RPE) is a monolayer of pigmented cells, which lies between the neural retina and the choriocapillars. The RPE cells play crucial roles in the maintenance and function of the retina and its photoreceptors. These include the formation of the blood-retinal barrier, absorption of stray light, supply of nutrients to the neural retina, regeneration of visual pigment, and uptake and recycling of shed outer segments of photoreceptors.

Retinal tissue may degenerate for a number of reasons. Among them are: artery or vein occlusion, diabetic retinopathy and retinopathy of prematurity, which are usually non-hereditary. There are hereditary diseases such as retinitis pigmentosa, retinoschisis, lattice degeneration, Best disease, Stargardt disease which also involve retinal tissue degeneration. A common retinal degeneration condition is age related macular degeneration (AMD). These conditions are characterized by progressive types of retinal degeneration.

RPE cells may potentially be used for cell replacement therapy of the degenerating RPE in retinal diseases mentioned above. It may be also used as a vehicle for the introduction of genes for the treatment of retinal degeneration diseases. These cells may also serve as an in vitro model of retinal degeneration diseases, as a tool for high throughput screening for a therapeutic effect of small molecules, and for the discovery and testing of new drugs for retinal degeneration diseases. RPE cells could also be used for basic research of RPE development, maturation, characteristics, properties, metabolism, immunogenicity, function and interaction with other cell types.

Human fetal and adult RPE has been used as an alternative donor source for allogeneic transplantation. However, practical problems in obtaining sufficient tissue supply and the ethical concerns regarding the use of tissues from aborted fetuses limit widespread use of these donor sources. Given these limitations in supply of adult and fetal RPE grafts, the potential of alternative donor sources have been studied. Human pluripotent stem cells provide significant advantages as a source of RPE cells for transplantation. Their pluripotent developmental potential may enable their differentiation into authentic functional RPE cells, and given their potential for infinite self renewal, they may serve as an unlimited donor source of RPE cells. Indeed, it has been demonstrated that human embryonic stem cells (hESCs) and human induced pluripotent stem cells (iPS) may differentiate into RPE cells in vitro, attenuate retinal degeneration and preserve visual function after subretinal transplantation to the Royal College of Surgeons (RCS) rat model of retinal degeneration that is caused by RPE dysfunction. Therefore, pluripotent stem cells may be an unlimited source for the production of RPE cells.

Current protocols for the derivation of RPE cells from pluripotent stem cells are labor intensive and time-consuming, yielding limited numbers of pigmented cells. New methods are required to produce RPE cells in quantities large enough that they can be used in the clinical setting.

Background art includes WO 2013/114360, WO 2008/129554 and WO 2013/184809.

SUMMARY OF THE INVENTION

According to an aspect of some embodiments of the present invention there is provided a method of generating retinal pigment epithelial (RPE) cells comprising:

(a) culturing human pluripotent stem cells in a human feeder cell-conditioned medium to obtain a cultured population of human pluripotent stem cells;

(b) culturing the cultured population of human pluripotent stem cells in a medium comprising a differentiating agent to obtain differentiating cells; and (c) culturing the differentiating cells in a medium comprising one or more members of the TGFβ superfamily, thereby generating the RPE cells.

According to an aspect of some embodiments of the present invention there is provided a method of generating RPE cells comprising:

(a) culturing human pluripotent stem cells in a human feeder cell-conditioned medium to obtain a cultured population of human pluripotent stem cells;

(b) culturing the cultured population of human pluripotent stem cells in a medium comprising a differentiating agent to obtain differentiating cells;

(c) culturing the differentiating cells in a medium comprising one or more members of the TGFβ superfamily to obtain RPE cells; and (d) culturing the RPE cells on an adherent surface to generate an expanded population of RPE cells.

According to an aspect of some embodiments of the present invention there is provided a method of treating a retinal disease comprising:

(a) culturing human pluripotent stem cells in a human feeder cell-conditioned medium to obtain a cultured population of human pluripotent stem cells;

(b) culturing the cultured population of human pluripotent stem cells in a medium comprising a differentiating agent to obtain differentiating cells;

(c) culturing the differentiating cells in a medium comprising one or more members of the TGFβ superfamily to obtain RPE cells;

(d) culturing the RPE cells on an adherent surface to generate an expanded population of RPE cells;

(e) harvesting the expanded population of RPE cells; and (f) transplanting the RPE cells into the subject's eye following the harvesting, thereby treating the disease.

According to an aspect of some embodiments of the present invention there is provided a population of RPE cells generated according to the method described herein.

According to an aspect of some embodiments of the present invention there is provided a method of treating a retinal disease or disorder in a subject in need thereof comprising administering a therapeutically effective amount of the RPE cells described herein to the subject thereby treating the retinal disease or disorder.

According to some embodiments of the invention, the method is effected on a large scale.

According to some embodiments of the invention, the feeder cell-conditioned medium is isolated from the feeder cells which are used to generate said feeder cell-conditioned medium.

According to some embodiments of the invention, the human feeder cell-conditioned medium comprises a human cord fibroblast conditioned medium.

According to some embodiments of the invention, the culturing of step (a) is effected in the absence of feeder cells.

According to some embodiments of the invention, the human cord fibroblast-conditioned medium is generated by culturing the human cord fibroblasts in a culture medium for at least two days.

According to some embodiments of the invention, the human cord fibroblasts are irradiated.

According to some embodiments of the invention, the conditioned medium comprises Nutristem.

According to some embodiments of the invention, the transplanting of the differentiated RPE cells is effected at the subretinal space of the eye.

According to some embodiments of the invention, the RPE cells are transplanted in a suspension, or as a monolayer of cells immobilized on a matrix or a substrate.

According to some embodiments of the invention, the human pluripotent stem cells comprise human embryonic stem cells.

According to some embodiments of the invention, the differentiating agent comprises nicotinamide.

According to some embodiments of the invention, the medium of step (b) is devoid of activin A.

According to some embodiments of the invention, the member of the TGFβ superfamily is selected from the group consisting of TGFβ1, TGFβ3 and activin A.

According to some embodiments of the invention, the medium of step (c) comprises nicotinamide and activin A.

According to some embodiments of the invention, the method further comprises a step of culturing the RPE cells in a medium comprising nicotinamide and devoid of activin A following step (c).

According to some embodiments of the invention, step (b) is effected under non-adherent conditions.

According to some embodiments of the invention, the non-adherent conditions comprise a non-adherent culture plate.

According to some embodiments of the invention, the non-adherent conditions comprise a non-adherent substrate.

According to some embodiments of the invention, step (b) comprises:
i) culturing the cultured population of human pluripotent stem cells in a medium comprising nicotinamide, in the absence of activin A; under non-adherent conditions to generate a cluster of cells comprising differentiating cells; and subsequently;
ii) culturing the differentiating cells of (i) in a medium comprising nicotinamide, in the absence of activin A under adherent conditions.

According to some embodiments of the invention, the method further comprises dissociating the cluster of cells prior to step (ii) to generate clumps of cells or a single cell suspension of cells.

According to some embodiments of the invention, step (a) is effected for about 1 week.

According to some embodiments of the invention, step (b) is effected for at least one week.

According to some embodiments of the invention, step (c) is effected for at least one week.

According to some embodiments of the invention, the method further comprises removing non-pigmented cells following step (c) and prior to step (d).

According to some embodiments of the invention, at least a portion of the culturing is effected under conditions wherein the atmospheric oxygen level is less than about 10%.

According to some embodiments of the invention, the culturing is effected under conditions wherein the atmospheric oxygen level is greater than about 10%.

According to some embodiments of the invention, the method further comprises expanding the human pluripotent stem cells on feeder cells prior to step (a).

According to some embodiments of the invention, the feeder cells comprise human cord fibroblasts.

According to some embodiments of the invention, the expanding is effected for at least two passages.

According to some embodiments of the invention, the expanding is effected for at least one week.

According to some embodiments of the invention, the retinal disease or disorder is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage due to damage caused by any one of photic, laser, inflammatory, infectious, radiation, neovascular or traumatic injury.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a diagrammatic illustration of a protocol for generating RPE cells according to embodiments of the present invention.

DESCRIPTION OF SPECIFIC EMBODIMENTS OF THE INVENTION

The present invention, in some embodiments thereof, relates to large scale production of retinal pigment epithelial cells from embryonic stem cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Human embryonic stem cells have been proposed as a cellular source for the generation of RPE cells. Two general approaches have been used to obtain retinal pigment epithelium (RPE) cells from hESCs, spontaneous differentiation and directed differentiation. In spontaneous differentiation, hESCs in flat colonies or in embryoid bodies (EBs) are allowed to spontaneously differentiate into a population of cells containing pigmented RPE cells. The directed differentiation method uses a number of factors to drive the differentiation of hESCs (which are present in spheroid bodies) to RPE cells see for example U.S. Pat. No. 8,956,866, the contents of which are incorporated herein by reference.

A key limitation of the protocol described therein is its low scale nature, which limits industrial bulk production. The initial step of RPE production described in U.S. Pat. No. 8,956,866 is based on culturing hESC colonies on cord feeders within single well culture dishes. The colonies are expanded by repetitive mechanical passages. This approach allows propagation at a low scale, is labor intensive and time consuming.

In the next step of the protocol described in U.S. Pat. No. 8,956,866, spheroid bodies (SBs) are produced by harvesting hESC clusters from the feeders and culturing under non-adherent conditions. This approach generates limited numbers of SBs and residual feeders in the SBs interfere with the downstream differentiation process. These limitations reduce the amount of pigmented RPE cells.

The present inventors now propose that the quantity of RPE cells generated by directed differentiation of hESCs in spheroid bodies can be enhanced by using feeder-free culture systems. More specifically, the present inventors propose that the embryonic stem cells should be cultured in feeder-free medium prior to the generation of spheroid bodies and further directed differentiation steps.

Whilst reducing the present invention to practice, the present inventors show that in the same time period, the number of undifferentiated hESCs that can be obtained is increased by a factor of at least three as compared to the protocol which relies solely on feeder cells for the expansion of hESCs. Furthermore, with one additional enzymatic passage of undifferentiated cells, the amount of hESC that can be obtained is increased by 13 fold. The amount of labor required for the expansion of hESCs was reduced dramatically. In addition, the present inventors found that the reproducibility in obtaining high levels of RPE cells using the feeder free cultures described herein was much greater as compared to the protocol which relies solely on feeder cells for the expansion of hESCs. Furthermore, the present inventors showed that when ESCs are cultured in non-feeder cell culture systems, the full protocol for generating RPE cells is equally effective under low and normal oxygen conditions, thereby rendering costly and elaborate steps such as manipulation of oxygen conditions unnecessary.

Thus, according to one aspect of the present invention there is provided a method of generating retinal pigment epithelial (RPE) cells comprising:

(a) culturing human pluripotent stem cells in a human feeder cell-conditioned medium to obtain a cultured population of human pluripotent stem cells, wherein said feeder cell-conditioned medium is isolated from the feeder cells which are used to generate said feeder cell-conditioned medium;

(b) culturing the cultured population of human pluripotent stem cells in a medium comprising a differentiating agent to obtain differentiating cells;

(c) culturing the differentiating cells in a medium comprising one or more members of the TGFβ superfamily, thereby generating the RPE cells.

"Retinal pigment epithelium cells", "RPE cells", "RPEs", which may be used interchangeably as the context allows, refers to cells of a cell type functionally similar to that of native RPE cells which form the pigment epithelium cell layer of the retina (e.g. upon transplantation within an eye, they exhibit functional activities similar to those of native RPE cells).

According to one embodiment, the RPE cell expresses at least one, two, three, four or five markers of mature RPE cells. Such markers include, but are not limited to CARLBP, RPE65, PEDF, PMEL17, Bestrophin and tyrosinase. Optionally, the RPE cell may also express a marker of an RPE progenitor—e.g. MITF. In another embodiment, the RPE cells express PAX-6. In another embodiment, the RPE cells express at least one marker of a retinal progenitor cell including, but not limited to Rx, OTX2, SIX3, SIX6 and LHX2.

As used herein the phrase "markers of mature RPE cells" refers to antigens (e.g. proteins) that are elevated (e.g. at least 2 fold, at least 5 fold, at least 10 fold) in mature RPE cells with respect to non RPE cells or immature RPE cells.

As used herein the phrase "markers of RPE progenitor cells" refers to antigens (e.g. proteins) that are elevated (e.g. at least 2 fold, at least 5 fold, at least 10 fold) in RPE progenitor cells with respect to non RPE cells.

According to another embodiment, the RPE cells have a morphology similar to that of native RPE cells which form the pigment epithelium cell layer of the retina i.e. pigmented and having a characteristic polygonal shape.

According to still another embodiment, the RPE cells are capable of treating diseases such as macular degeneration.

According to still another embodiment, the RPE cells fulfill at least 1, 2, 3, 4 or all of the requirements listed herein above.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPSCs), adult stem cells, mesenchymal stem cells and hematopoietic stem cells.

According to a particular embodiment, the RPE cells are generated from pluripotent stem cells (e.g. ESCs or iPSCs).

Induced pluripotent stem cells (iPSCs) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation. The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by a procedure in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Reubinoff et al., Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention. Human ES cells can be purchased from the NIH human embryonic stem cells registry [Hypertext Transfer Protocol://grants (dot) nih (dot) gov/stem_cells/registry/current(dot)htm]. Non-limiting examples of commercially available embryonic stem cell lines are HAD-C102, ESI, BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

According to a specific embodiment, the embryonic stem cell line is HAD-C102 or ESI.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Yet another method for preparing ES cells is by parthenogenesis. The embryo is also not destroyed in the process.

According to this aspect of the present invention, the human pluripotent stem cells are cultured in conditioned medium prior to the first stage of directed differentiation. The feeder cell-conditioned medium is isolated from (or collected from) the feeder cells which are used to generate said feeder cell-conditioned medium. Thus, the embryonic stem cells are preferably cultured in a different container to the container used for generating the cell-conditioned medium. Although, trace amounts of feeder cells may be comprised in the conditioned medium, preferably, this culturing step is typically carried out in the absence of feeder cells. Culturing the human pluripotent stem cells is typically effected for at least one day, more preferably at least two days e.g. two days, three days, four days, five days, six days or seven days. Preferably, the culturing in conditioned medium is not carried out for more than 21 days, e.g. not more than 14 days. According to a particular embodiment, the culturing is effected on a dish or a flask (e.g. T75 flask or T175 flask). The solid surface may be coated with a non-adherent substrate such as fibronectin, laminin, polyD-lysine or gelatin. After a suitable length of time, hESC colonies may be removed from the solid surface using a suitable agent—for example using collagenase A, dispase, TrypLE select, or EDTA.

Conditioned Medium

Conditioned medium is the growth medium of a monolayer cell culture (i.e., feeder cells) present following a certain culturing period. The conditioned medium includes growth factors and cytokines secreted by the monolayer cells in the culture.

The conditioned medium of the present invention can be collected from a variety of human cells forming monolayers in culture. Examples include human foreskin conditioned medium, human embryonic fibroblasts conditioned medium, human fallopian epithelial cells conditioned medium, and human cord fibroblast conditioned medium.

Particularly suitable conditioned medium are those derived from human cells, such as human cord fibroblast-conditioned medium which is produced by culturing human cord fibroblast cells in a growth medium under conditions suitable for producing the conditioned medium.

According to a specific embodiment, the feeder cells are mitotically inactivated by irradiation. Other methods of inactivation may be used such as Mitomycin treatment.

Such a growth medium can be any medium suitable for culturing feeder cells. The growth medium can be supplemented with nutritional factors, such as amino acids, (e.g., L-glutamine), anti-oxidants (e.g., beta-mercaptoethanol) and growth factors, which benefit stem cell growth in an undifferentiated state. Serum and serum replacements are added at effective concentration ranges as described elsewhere (U.S. patent application Ser. No. 10/368,045).

Feeder cells are cultured in the growth medium for sufficient time to allow adequate accumulation of secreted factors to support stem cell proliferation in an undifferentiated state. Typically, the medium is conditioned by culturing for 4-48 hours at 37° C. However, the culturing period can be scaled by assessing the effect of the conditioned medium on stem cell growth and differentiation.

According to a particular embodiment the conditioned medium is prepared by seeding irradiated human cord cells in a medium (e.g. DMEM) in the presence of human serum for about 5-24 hours. Longer culture periods up to about 7 days may also be effective. The cells are then cultured in a medium (e.g. Nutristem) in the absence of human serum for another 24 hours. The second medium may comprise human serum albumin. Furthermore, the second medium may comprise growth factors such as basic FGF and factors from the TGFβ superfamily. According to a particular embodiment, the culture dishes on which the conditioned medium is prepared are not coated with gelatin.

According to another embodiment, the culture media which are used to prepare the conditioned medium do not comprise fibroblast growth factor (FGF) or TGFβ superfamily factors. Selection of culture apparatus for conditioning the medium is based on the scale and purpose of the conditioned medium. Large-scale production preferably involves the use of dedicated devices. According to a particular embodiment, the conditioned medium is prepared in flasks. Continuous cell culture systems are reviewed in Furey (2000) Genetic Eng. News 20:10.

Following accumulation of adequate factors in the medium, growth medium (i.e., conditioned medium) is separated from the feeder cells and collected. It will be appreciated that the feeder cells can be used repeatedly to condition further batches of medium over additional culture periods, provided that the cells retain their ability to condition the medium.

Preferably, the conditioned medium is sterilized (e.g., filtration using a 20 μM filter) prior to use. The conditioned medium of some embodiments of the invention may be applied directly on stem cells or extracted to concentrate the effective factor such as by salt filtration. For future use, conditioned medium is preferably stored frozen at −80° C.

It will be appreciated that the present invention contemplates additional steps prior to the feeder-free conditioned medium step which aid in the expansion of the pluripotent stem cells.

Thus, according to a particular embodiment, the ESCs are expanded on feeders prior to the feeder-free conditioned medium step. Exemplary feeder layer based cultured contemplated by the present invention are described herein below. The expansion is typically effected for at least two days, three days, four days, five days, six days or seven days. The expansion is effected for at least 1 passage, or at least 2 passages.

Human Cord Feeder-Layer—

Human cord fibroblasts may be expanded in Dulbecco's Modified Eagle's Medium (e.g. DMEM, SH30081.01, Hyclone) supplemented with human serum (e.g. 20%). Preferably the human cord cells are irradiated. This may be effected using methods known in the art (e.g. Gamma cell, 220 Exel, MDS Nordion 3,500 rads). Once sufficient cells are obtained they may be frozen (e.g. cryopreserved). For expansion of ESCs, the human cord fibroblasts are typically seeded on a solid surface (e.g. T75 or T175 flasks) optionally coated with an adherent substrate such as gelatin (e.g. recombinant human gelatin (RhG100-001, Fibrogen) at a concentration of 25-30000 cells/cm$^2$ in DMEM (e.g. SH30081.01, Hyclone) supplemented with about 20% human serum. hESCs are typically plated on top of the feeder cells 1-4 days later in a supportive medium (e.g. Nutristem). Additional factors may be added to the medium to prevent differentiation of the ESCs such as bFGF and TGF-β. Once a sufficient amount of hESCs are obtained, the cells may be mechanically disrupted (e.g. by using a sterile tip or a disposable sterile stem cell tool; 14602 Swemed). Alternatively, the cells may be removed by enzymatic treatment (e.g. collagenase A, or Tryple Select). This process may be repeated several times to reach the necessary amount of hESC. According to a particular embodiment, following the first round of expansion, the hESCs are removed using Tryple Select and following the second round of expansion, the hESCs are removed using collagenase A.

Human Embryonic Fibroblasts or Adult Fallopian Epithelial Cells as Feeder Cell Layers—

Human ES cells can be grown and maintained using human embryonic fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6].

Foreskin Feeder Layers—

Human ES cells can be cultured on human foreskin feeder layer as disclosed in U.S. patent application Ser. No. 10/368, 045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers.

Preferably, the feeder cell type which is used for generation of the conditioned medium is identical to the feeder cell type used for the initial expansion of the hESCs. Thus, for example if human cord fibroblasts are used to generate the conditioned medium, then initial expansion of the hESCs should be carried out on human cord fibroblast feeders.

Following culture in the human feeder cell-conditioned medium, the ESCs are subjected to directed differentiation using a differentiating agent.

In one exemplary differentiation protocol, the embryonic stem cells are differentiated towards the RPE cell lineage using a first differentiating agent and then further differentiated towards RPE cells using a member of the transforming growth factor-ß (TGFß) superfamily, (e.g. TGFβ1, TGFβ2, and TGFβ3 subtypes, as well as homologous ligands including activin (e.g., activin A, activin B, and activin AB), nodal, anti-mullerian hormone (AMH), some bone morphogenetic proteins (BMP), e.g. BMP2, BMP3, BMP4, BMP5, BMP6, and BMP7, and growth and differentiation factors (GDF)). According to a specific embodiment, the member of the transforming growth factor-ß (TGFß) superfamily is activin A—e.g. between 20-200 ng/ml e.g. 100-180 ng/ml.

According to a particular embodiment, the first differentiating agent is nicotinamide (NA)—e.g. between 1-100 mM, 5-50 mM, 5-20 mM, e.g. 10 mM.

According to another embodiment, the first differentiating agent is 3-aminobenzamide.

NA, also known as "niacinamide", is the amide derivative form of Vitamin B3 (niacin) which is thought to preserve and improve beta cell function. NA has the chemical formula $C_6H_6N_2O$. NA is essential for growth and the conversion of foods to energy, and it has been used in arthritis treatment and diabetes treatment and prevention.

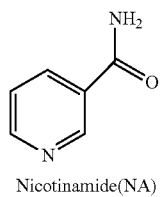

Nicotinamide(NA)

According to a particular embodiment, the nicotinamide is a nicotinamide derivative or a nicotinamide mimic. The term "derivative of nicotinamide (NA)" as used herein denotes a compound which is a chemically modified derivative of the natural NA. In one embodiment, the chemical modification may be a substitution of the pyridine ring of the basic NA structure (via the carbon or nitrogen member of the ring), via the nitrogen or the oxygen atoms of the amide moiety. When substituted, one or more hydrogen atoms may be replaced by a substituent and/or a substituent may be attached to a N atom to form a tetravalent positively charged nitrogen. Thus, the nicotinamide of the present invention includes a substituted or non-substituted nicotinamide. In another embodiment, the chemical modification may be a deletion or replacement of a single group, e.g. to form a thiobenzamide analog of NA, all of which being as appreciated by those versed in organic chemistry. The derivative in the context of the invention also includes the nucleoside derivative of NA (e.g. nicotinamide adenine). A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives (WO05/014549). Other exemplary nicotinamide derivatives are disclosed in WO01/55114 and EP2128244.

Nicotinamide mimics include modified forms of nicotinamide, and chemical analogs of nicotinamide which recapitulate the effects of nicotinamide in the differentiation and maturation of RPE cells from pluripotent cells. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

According to a particular embodiment, the differentiation is effected as follows:

a) culture of ESCs in a medium comprising a first differentiating agent (e.g. nicotinamide); and b) culture of cells obtained from step a) in a medium comprising a member of the TGFß superfamily (e.g. activin A) and the first differentiating agent (e.g. nicotinamide).

Preferably step (a) is effected in the absence of the member of the TGFβ superfamily.

The above described protocol may be continued by culturing the cells obtained in step b) in a medium comprising the first differentiating agent (e.g. nicotinamide), but devoid of a member of the TGFß superfamily (e.g. activin A). This step is referred to herein as step (c).

The above described protocol is now described in further detail, with additional embodiments.

Step (a): The differentiation process is started once sufficient quantities of ESCs are obtained. They are typically removed from the conditioned medium cell culture (e.g. by using collagenase A, dispase, TrypLE select, EDTA) and plated onto a non-adherent substrate (e.g. cell culture plate such as an agarose-coated culture dish such as Hydrocell, or petri bacteriological dishes) in the presence of nicotinamide (and the absence of activin A). Exemplary concentrations of nicotinamide are between 1-100 mM, 5-50 mM, 5-20 mM, e.g. 10 mM. Once the cells are plated onto the non-adherent substrate (e.g. cell culture plate), the cell culture may be referred to as a cell suspension, preferably free floating clusters in a suspension culture, i.e. aggregates of cells derived from human embryonic stem cells (hESCs). The cell clusters do not adhere to any substrate (e.g. culture plate, carrier). Sources of free floating stem cells were previously described in WO 06/070370, which is herein incorporated by reference in its entirety. This stage may be effected for a minimum of 1 day, more preferably two days, three days, 1 week or even 14 days. Preferably, the cells are not cultured for more than 3 weeks in suspension together with the nicotinamide e.g. between 1-100 mM, 5-50 mM, 5-20 mM, e.g. 10 mM (and in the absence of activin).

In one embodiment, the cells are cultured for 6-8 days in suspension together with the nicotinamide e.g. between 1-100 mM, 5-50 mM, 5-20 mM, e.g. 10 mM (and in the absence of activin A).

According to one embodiment, when the cells are cultured on the non-adherent substrate e.g. cell culture plates, the atmospheric oxygen conditions are 20%. However, manipulation of the atmospheric oxygen conditions is also contemplated such that the atmospheric oxygen percent is less than about 20%, 15%, 10%, 9%, 8%, 7%, 6% or even less than about 5% (e.g. between 1%-20%, 1%-10% or 0-5%).

According to a particular embodiment, the cells are cultured on the non-adherent substrate initially under normal atmospheric oxygen conditions and then lowered to less than normal atmospheric oxygen conditions.

Examples of non-adherent cell culture plates include those manufactured by Nunc (e.g. Hydrocell Cat No. 174912).

Typically, the clusters comprise at least 50-500,000, 50-100,000, 50-50,000, 50-10,000, 50-5000, 50-1000 cells. According to one embodiment, the cells in the clusters are not organized into layers and form irregular shapes. In one embodiment, the clusters are devoid of pluripotent embryonic stem cells. In another embodiment, the clusters comprise small amounts of pluripotent embryonic stem cells (e.g. no more than 5%, or no more than 3% (e.g. 0.01-2.7%) cells that co-express OCT4 and TRA 1-60 at the protein level). Typically, the clusters comprise cells that have been partially differentiated under the influence of nicotinamide. Such cells primarily express neural and retinal precursor markers such as PAX6, Rax, Six3 and/or CHX10 as well as markers of progenitors of other lineages such as alpha-feto protein, MIXL1 and Brachyury.

The clusters may be dissociated using enzymatic or non-enzymatic methods (e.g., mechanical) known in the art. According to one embodiment, the cells are dissociated such that they are no longer in clusters—e.g. aggregates or clumps of 2-100,000 cells, 2-50,000 cells, 2-10,000 cells, 2-5000 cells, 2-1000 cells, 2-500 cells, 2-100 cells, 2-50 cells. According to a particular embodiment, the cells are in a single cell suspension.

The cells (e.g. dissociated cells) are then plated on an adherent substrate and cultured in the presence of nicotinamide e.g. between 1-100 mM, 5-50 mM, 5-20 mM, e.g. 10 mM (and the absence of activin A). This stage may be effected for a minimum of 1 day, more preferably two days, three days, 1 week or even 14 days. Preferably, the cells are not cultured for more than 3 weeks in the presence of nicotinamide (and in the absence of activin). In an exemplary embodiment, this stage is effected for 6-7 days.

According to one embodiment, when the cells are cultured on the adherent substrate e.g. laminin, the atmospheric oxygen conditions are 20%. They may be manipulated such that the percentage is less than about 20%, 15%, 10%, more preferably less than about 9%, less than about 8%, less than about 7%, less than about 6% and more preferably about 5% (e.g. between 1%-20%, 1%-10% or 0-5%).

According to a particular embodiment, the cells are cultured on the adherent substrate initially under normal atmospheric oxygen conditions and then lowered to less than normal atmospheric oxygen conditions.

Examples of adherent substrates include but are not limited to fibronectin, laminin, polyD-lysine and gelatin.

Step (b): Following the first stage of directed differentiation, (step a; i.e. culture in the presence of nicotinamide (e.g. between 1-100 mM, 5-50 mM, 5-20 mM, e.g. 10 mM), the semi-differentiated cells are then subjected to a further stage of differentiation on an adherent substrate—culturing in the presence of activin A (e.g. 100-200 ng/ml—for example 140 ng/ml, 150 ng/ml, 160 ng/ml or 180 ng/ml). Nicotinamide may be added at this stage too (e.g. between 1-100 mM, 5-50 mM, 5-20 mM, e.g. 10 mM).

This stage may be effected for 1 day to 10 weeks, 3 days to 10 weeks, 1 week to 10 weeks, one week to eight weeks, one week to four weeks, for example for at least one day, at least two days, at least three days, at least 5 days, at least one week, at least two weeks, at least three weeks, at least four weeks, at least five weeks, at least six weeks, at least seven weeks, at least eight weeks, at least nine weeks, at least ten weeks.

According to a specific embodiment this stage is effected for about two weeks. This stage of differentiation may be effected at low or normal atmospheric oxygen conditions, as detailed herein above.

Step (c): Following the second stage of directed differentiation (i.e. culture in the presence of nicotinamide and activin A on an adherent substrate; step (b)), the further differentiated cells are optionally subjected to a subsequent stage of differentiation on the adherent substrate—culturing in the presence of nicotinamide (e.g. between 1-100 mM, 5-50 mM, 5-20 mM, e.g. 10 mM), in the absence of activin A. This stage may be effected for at least one day, 2, days, 5 days, at least one week, at least two weeks, at least three weeks or even four weeks. Preferably this stage is effected for about one week. This stage of differentiation may also be carried out at low or normal atmospheric oxygen conditions, as detailed herein above.

The basic medium in which the ESCs are differentiated is any known cell culture medium known in the art for supporting cells growth in vitro, typically, a medium comprising a defined base solution, which includes salts, sugars, amino acids and any other nutrients required for the maintenance of the cells in the culture in a viable state. According to a specific embodiment, the basic medium is not a conditioned medium. Non-limiting examples of commercially available basic media that may be utilized in accordance with the invention comprise Nutristem (without bFGF and TGFβ for ESC differentiation, with bFGF and TGFβ for ESC expansion) Neurobasal™, KO-DMEM, DMEM, DMEM/F12, Cellgro™ Stem Cell Growth Medium, or X-Vivo™ The basic medium may be supplemented with a variety of agents as known in the art dealing with cell cultures. The following is a non-limiting reference to various supplements that may be included in the culture system to be used in accordance with the present disclosure:

serum or with a serum replacement containing medium, such as, without being limited thereto, knock out serum replacement (KOSR), Nutridoma-CS, TCH™, N2, N2 derivative, or B27 or a combination;

an extracellular matrix (ECM) component, such as, without being limited thereto, fibronectin, laminin, collagen and gelatin. The ECM may then be used to carry the one or more members of the TGFβ superfamily of growth factors;

an antibacterial agent, such as, without being limited thereto, penicillin and streptomycin;

non-essential amino acids (NEAA), neurotrophins which are known to play a role in promoting the survival of SCs in culture, such as, without being limited thereto, BDNF, NT3, NT4.

According to a preferred embodiment, the medium used for differentiating the ESCs is Nutristem medium (e.g. Biological Industries, 06-5102-01-1A).

According to a particular embodiment differentiation and expansion of ESCs is effected under xeno free conditions.

According to one embodiment, the proliferation/growth medium is devoid of xeno contaminants i.e. free of animal derived components such as serum, animal derived growth factors and albumin. Thus, according to this embodiment, the culturing is performed in the absence of xeno contaminants.

Other methods for culturing ESCs under xeno free conditions are provided in U.S. Patent Application No. 20130196369, the contents of which are incorporated in their entirety.

The preparations comprising RPE cells may be prepared in accordance with Good Manufacturing Practices (GMP) (e.g., the preparations are GMP-compliant) and/or current Good Tissue Practices (GTP) (e.g., the preparations may be GTP-compliant).

During differentiation steps, the embryonic stem cells may be monitored for their differentiation state. Cell differentiation can be determined upon examination of cell or tissue-specific markers which are known to be indicative of differentiation.

Tissue/cell specific markers can be detected using immunological techniques well known in the art [Thomson J A et al., (1998). Science 282: 1145-7]. Examples include, but are not limited to, flow cytometry for membrane-bound or intracellular markers, immunohistochemistry for extracellular and intracellular markers and enzymatic immunoassay, for secreted molecular markers.

Once the cells are promoted into the RPE fate, the RPE cells may be selected and/or expanded.

According to a particular embodiment, the selection is based on a negative selection—i.e. removal of non-RPE cells. This may be done mechanically by removal of non-pigmented cells or by use of surface markers.

According to another embodiment, the selection is based on a positive selection i.e. selection of pigmented cells. This may be done by visual analysis or use of surface markers.

According to still another embodiment, the selection is based first on a negative selection and then on a positive selection.

Expansion of RPE cells may be effected on an extra cellular matrix, e.g. gelatin, collagen, fibronectin or laminin (e.g laminin 521) and poly-D-lysine. For expansion, the cells may be cultured in serum-free KOM, serum comprising medium (e.g. DMEM+20%) or Nutristem medium (06-5102-01-1A Biological Industries). Under these culture conditions, after passage and plating at low density (about 130,000 cells/cm$^2$), the pigmented cells reduce pigmentation and acquire a fibroid-like morphology. Following further prolonged culture and proliferation into high-density cultures, the cells re-acquire the characteristic polygonal shape morphology and increase pigmentation of RPE cells.

In one embodiment, the expanding is effected in the presence of nicotinamide (e.g. between 1-100 mM, 5-50 mM, 5-20 mM, e.g. 10 mM), and in the absence of activin A.

The RPE cells may be expanded in suspension or in a monolayer. The expansion of the RPE cells in monolayer cultures may be modified to large scale expansion in bioreactors by methods well known to those versed in the art.

According to one embodiment, the expansion phase is effected for at least one week, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-8 weeks.

According to still another embodiment, the cells are passaged at least 1 time during the expansion phase, at least twice during the expansion phase, at least three times during the expansion phase, at least four times during the expansion phase, at least five times during the expansion phase, or at least six times during the expansion phase.

The population of RPE cells generated according to the methods described herein may be characterized according to a number of different parameters.

Thus, for example, the RPE cells obtained may be polygonal in shape and pigmented.

Harvesting of the expanded population of RPE cells may be effected using methods known in the art (e.g. using an enzyme such as trypsin).

Following harvesting, the expanded population of RPE cells may optionally be cryopreserved using methods known in the art.

The method of this aspect of the present invention may be effected on a large scale.

The term "large-scale" refers to a production process involving at least one culture vessel of at least 100 mL. In preferred embodiments, however, the scale is typically at least 250 mL, such as at least 500 mL, e.g. at least 1 L or even 5 L or more. The term "large-scale" may be used interchangeably with the terms "industrial-scale" and "production-scale".

It will be appreciated that the cell populations disclosed herein are devoid of undifferentiated human embryonic stem cells. According to one embodiment, less than 1:250,000 cells are Oct4$^+$TRA-1-60$^+$ cells, as measured for example by FACS. The cells also have down regulated (by more than 5,000 fold) expression of GDF3 or TDGF as measured by PCR.

The RPE cells of this aspect of the present invention do not express embryonic stem cell markers. Said one or more embryonic stem cell markers may comprise OCT-4, NANOG, Rex-1, alkaline phosphatase, Sox2, TDGF-beta, SSEA-3, SSEA-4, TRA-1-60, and/or TRA-1-81.

The RPE preparations may be substantially purified, with respect to non-RPE cells, comprising at least about 75%, 80%, 85%, 90%, 91%, 92%, 93%, 94%, 95%, 96%, 97%, 98%, 99%, or 100% RPE cells. The RPE cell preparation may be essentially free of non-RPE cells or consist of RPE cells. For example, the substantially purified preparation of RPE cells may comprise less than about 25%, 20%, 15%, 10%, 9%, 8%, 7%, 6%, 5%, 4%, 3%, 2%, or 1% non-RPE cell type. For example, the RPE cell preparation may comprise less than about 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-RPE cells.

The RPE cell preparations may be substantially pure, both with respect to non-RPE cells and with respect to RPE cells of other levels of maturity. The preparations may be substantially purified, with respect to non-RPE cells, and enriched for mature RPE cells. For example, in RPE cell preparations enriched for mature RPE cells, at least about 30%, 40%, 45%, 50%, 55%, 60%, 65%, 70%, 75%, 80%, 85%, 90%, 91%, 92%, 93%, 94%, 95%, 96%, 97%, 98%, 99%, 99%, or 100% of the RPE cells are mature RPE cells. The preparations may be substantially purified, with respect to non-RPE cells, and enriched for differentiated RPE cells rather than mature RPE cells. For example, at least about 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the RPE cells may be differentiated RPE cells rather than mature RPE cells.

The preparations described herein may be substantially free of bacterial, viral, or fungal contamination or infection, including but not limited to the presence of HIV I, HIV 2, HBV, HCV, HAV, CMV, HTLV 1, HTLV 2, parvovirus B19, Epstein-Barr virus, or herpesvirus 1 and 2, SV40, HHV5, 6, 7, 8, CMV, polyoma virus, HPV, Enterovirus. The preparations described herein may be substantially free of mycoplasma contamination or infection.

Another way of characterizing the cell populations disclosed herein is by marker expression, Thus, for example, at least 80%, 85%, 90%, 95% or 100% of the cells express Bestrophin 1, as measured by immunostaining. According to one embodiment, between 85-100% of the cells express bestrophin.

According to another embodiment, at least 80%, 85%, 87%, 89%, 90%, 95%, 97% or 100% of the cells express Microphthalmia-associated transcription factor (MITF), as measured by immunostaining. For example, between 85-100% of the cells express MITF.

According to another embodiment, at least 80% 85%, 87%, 89%, 90%, 95%, 97% or 100% of the cells express paired box gene 6 (PAX-6) as measured by immunostaining or FACS.

According to another embodiment, at least 80%, 85%, 87%, 89%, 90%, 95%, 97% or 100% of the cells express cellular retinaldehyde binding protein (CRALBP), as measured by immunostaining. For example, between 85-100% of the cells express CRALBP.

According to another embodiment, at least 80%, 85%, 87%, 89%, 90%, 95%, 97% or 100% of the cells express retinal pigment epithelium-specific protein 65 kDa (RPE65), as measured by immunostaining. For example, between 85-100% of the cells express RPE65.

The RPE cells typically co-express markers indicative of terminal differentiation, e.g. bestrophin 1, premelanosome protein (PMEL17), CRALBP and/or RPE65.

It would be well appreciated by those versed in the art that the derivation of RPE cells is of great benefit. They may be used as an in vitro model for the development of new drugs to promote their survival, regeneration and function. RPE cells may serve for high throughput screening for compounds that have a toxic or regenerative effect on RPE cells. They may be used to uncover mechanisms, new genes, soluble or membrane-bound factors that are important for the development, differentiation, maintenance, survival and function of photoreceptor cells.

The RPE cells may also serve as an unlimited source of RPE cells for transplantation, replenishment and support of malfunctioning or degenerated RPE cells in retinal degenerations. Furthermore, genetically modified RPE cells may serve as a vector to carry and express genes in the eye and retina after transplantation.

Eye conditions for which the RPE cells may serve as therapeutics include, but are not limited to retinal diseases or disorders generally associated with retinal dysfunction, retinal injury, and/or loss of retinal pigment epithelium. A non-limiting list of conditions which may be treated in accordance with the invention comprises retinitis pigmentosa, lebers congenital amaurosis, hereditary or acquired macular degeneration, age related macular degeneration (AMD), dry AMD, Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

Subjects which may be treated include primate (including humans), canine, feline, ungulate (e.g., equine, bovine, swine (e.g., pig)), avian, and other subjects. Humans and non-human animals having commercial importance (e.g., livestock and domesticated animals) are of particular interest. Exemplary mammals which may be treated include, canines; felines; equines; bovines; ovines; rodentia, etc. and primates, particularly humans. Non-human animal models, particularly mammals, e.g. primate, murine, lagomorpha, etc. may be used for experimental investigations.

The RPE cells generated as described herein may be transplanted to various target sites within a subject's eye. In accordance with one embodiment, the transplantation of the RPE cells is to the subretinal space of the eye, which is the normal anatomical location of the RPE (between the photoreceptor outer segments and the choroids). In addition, dependent upon migratory ability and/or positive paracrine effects of the cells, transplantation into additional ocular compartments can be considered including the vitreal space, inner or outer retina, the retinal periphery and within the choroids.

The number of viable cells that may be administered to the subject are typically between $50,000$-$5 \times 10^6$ per injection.

The cells are typically formulated in a carrier (e.g. an isotonic solution and/or a saline) such as BSS Plus™. Other contemplated solutions include cryopreservation solutions such as Cryostor 5 or Cryostor 2. The carrier may optionally comprise additional factors that support RPE engraftment, integration, survival, potency etc.

The transplantation may be performed by various techniques known in the art. Methods for performing RPE transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

The step of administering may comprise intraocular administration of the RPE cells into an eye in need thereof. The intraocular administration may comprise injection of the RPE cells into the subretinal space.

In accordance with one embodiment, transplantation is performed via pars plana vitrectomy surgery followed by delivery of the cells through a small retinal opening into the sub-retinal space or by direct injection.

The RPE cells may be transplanted in various forms. For example, the RPE cells may be introduced into the target site in the form of single cell suspension, with matrix or adhered onto a matrix or a membrane, extracellular matrix or substrate such as a biodegradable polymer or a combination. The RPE cells may also be transplanted together (co-transplantation) with other retinal cells, such as with photoreceptors.

The effectiveness of treatment may be assessed by different measures of visual and ocular function and structure, including, among others, best corrected visual acuity (BCVA), retinal sensitivity to light as measured by perimetry or microperimetry in the dark and light-adapted states, full-field, multi-focal, focal or pattern elecroretinography ERG), contrast sensitivity, reading speed, color vision, clinical biomicroscopic examination, fundus photography, optical coherence tomography (OCT), fundus auto-fluorescence (FAF), infrared and multicolor imaging, fluorescein or ICG angiography, and additional means used to evaluate visual function and ocular structure.

The subject may be administered corticosteroids prior to or concurrently with the administration of the RPE cells, such as prednisolone or methylprednisolone, Predforte.

According to another embodiment, the subject is not administered corticosteroids prior to or concurrently with the administration of the RPE cells, such as prednisolone or methylprednisolone, Predforte.

Immunosuppressive drugs may be administered to the subject prior to, concurrently with and/or following treatment.

The immunosuppressive drug may belong to the following classes:

Glucocorticoids, Cytostatics (e.g. alkylating agent or antimetabolite), antibodies (polyclonal or monoclonal), drugs acting on immunophils (e.g. ciclosporin, Tacrolimus or Sirolimus). Additional drugs include interferons, opioids, TNF binding proteins, mycophenolate and small biological agents.

Examples of immunosuppressive drugs include: mesenchymal stem cells, anti-lymphocyte globulin (ALG) polyclonal antibody, anti-thymocyte globulin (ATG) polyclonal antibody, azathioprine, BAS 1 L1X1MAB® (anti-I L-2Ra receptor antibody), cyclosporin (cyclosporin A), DACLIZUMAB® (anti-I L-2Ra receptor antibody), everolimus, mycophenolic acid, RITUXIMAB® (anti-CD20 antibody), sirolimus, tacrolimus, Tacrolimus and or Mycophenolate mofetil.

Antibiotics may be administered to the subject prior to, concurrently with and/or following treatment. Examples of antibiotics include Oflox, Gentamicin, Chloramphenicol, Tobrex, Vigamox or any other topical antibiotic preparation authorized for ocular use.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed.

(1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods
Short Protocol
Preparation of Conditioned Medium:

T75 flasks were seeded with irradiated cord cells ($2.3 \times 10^6$ w/o gelatin) in DMEM+20% Human serum medium. After 5-24 hr, the medium was replaced with Nutristem+HSA for conditioning. After 16 to 72 hour of conditioning the medium was harvested and replaced by fresh medium. According to this methodology, sequential conditioning of medium could be performed 3-4 times per week.

Culture of hESCs in Conditioned Medium (Experiments CM 1, 3, 4):

hESC colonies (day 8) of four center-well plates were treated with collagenase A, harvested and gently triturated. The hESCs were seeded in T75 flask coated with gelatin and cultured with conditioned medium from the cord flask. The conditioned medium was replaced every 1-3 days. After 6-7 days the flask was full with hESC colonies, which were harvested with collagenase A, to form purified culture of feeder free SBs.

Expansion of hESCs (Experiment CM11, 12):

Four center well plates were harvested as above and the cells were plated in T75 flask pre-seeded with cord feeders ($2.3 \times 10^6$ per flask). Following one week of culture in Nutristem+HSA, hESCs were harvested with Tryple Select (diluted 1:1 with PBS in some experiments) and split, seeding $2 \times 10^6$ hESC per T175 flask, pre-seeded with cord feeders ($5 \times 10^6$ per flask). For further expansion (experiment CM 12), after a week of culture in Nutristem+HSA, hESCs were harvested and split as above, seeding $2 \times 10^6$ hESC per T175 flask.

For transfer to feeder-free culture in conditioned medium, the hESC, after one week culture in T175 flasks as above were harvested using collagenase A, and a quarter of them was seeded into feeder-free T175 flask and cultured in conditioned medium. After 7 days the flask was full with hESC colonies, which were harvested with collagenase A.

Generation of RPE Cells:

The hESC clusters harvested from the conditioned medium culture conditions were cultured in 6 cm hydrocell dishes and incubated with Nutristem Minus medium (Nutristem without growth factors supplementation) with the addition of 10 mM nicotinamide, under low oxygen conditions (5% $O_2$; experiments CM1, CM3) or normal oxygen (20% $O_2$; experiments CM4, CM9, CM11, CM12). Following 7-13 days (CM1-7 days, CM3-13 days, CM4-9 days, CM11-7 days) spheroid bodies (SBs) were triturated and seeded on human laminin 511 coated plates, and maintained for one week with nicotinamide (10 mM) and two weeks with nicotinamide (10 mM) and activin A (140 ng/ml) (under low or normal oxygen conditions).

When pigmented areas appeared, the non-pigmented regions were removed by Tryple Select treatment (6-20 min in 37° C.) combined with mechanical separation. The pigmented cells were further separated from the dish by gentle blow of medium from pipette, harvested, counted and seeded as P0 on gelatin coated 6 well plates with Nutristem Minus media under normal oxygen conditions. After two weeks the pigmented cells were passaged with Tryple Select into flasks w/o gelatin and cultured with Nutristem Minus media (P1). After additional two weeks an additional similar passage was performed (P2).

Schematic presentation of the procedures of experiment CM11 appears in FIG. 1.

Table 1 summarizes the results of experiments CM1, CM3, CM4, CM11. It presents the total number of RPE cells at each stage along the protocol. The yield of RPE cells per one well at P0 is similar between the four experiments (fourth column). The average amount of RPE cells per one well is $5.64 \pm 0.68 \times 10^6$ (n=4). The small SD indicates that the variation between the experiments is very low.

TABLE 1

The amount of RPE cells harvested along the protocol

| Exp No. | Harvest of RPE cells from Laminin (6 well plate) | Harvest of RPE at P0 (6 well plate) | RPE at P0 Number of cells per one well | Harvest of RPE P1 (T75 flask)* | Harvest of RPE P2 (T175 flask)* |
|---|---|---|---|---|---|
| CM1 5% $O_2$ | Harvest of one well $1.1 \times 10^6$ | Harvest of 2 wells $12.9 \times 10^6$ | $6.45 \times 10^6$ | $45.4 \times 10^6$ | $86 \times 10^6$ |
| CM3 5% $O_2$ | Harvest of 3 well $2 \times 10^6$ | Harvest of 3 wells $14.8 \times 10^6$ | $4.93 \times 10^6$ | $38 \times 10^6$ | $138 \times 10^6$ |
| CM4 20% $O_2$ | Harvest of 3 well $2 \times 10^6$ | Harvest of 3 wells $15.8 \times 10^6$ | $5.26 \times 10^6$ | $50 \times 10^6$ | $133 \times 10^6$ |
| CM11 20% $O_2$ Large scale of hESC | Harvest of 6 well $11 \times 10^6$ | Harvest of 12 wells $71 \times 10^6$ | $5.92 \times 10^6$ | T175 flask $121 \times 10^6$ | $68 \times 10^6$ |

Table 2 provides a comparison between the amounts of the harvested RPE cells generated using the protocols described herein (CM1, CM3, CM4, CM11) and another protocol previously used which is similar to that disclosed herein from the stage of differentiation of floating hESC clusters in the presence of nicotinamide.

The amount of RPE cells that were obtained from starting material of undifferentiated hESC cultured in four center well plates in CM1, CM3, CM4 experiments (fifth column) was reproducible ($14.5\pm1.2\times10^6$) with low SD, as opposed to the previous protocol that did not include a culture step in conditioned medium (RPE2, 3, 5 and 6; $50.4\pm22.6\times10^6$).

The average yield of RPE cells relative to the amount of initial undifferentiated hESC in center well plates (seven and eight columns), was two fold higher ($3.6\times10^6$ versus $1.7\times10^6$), in CM1, CM3, CM4 experiments, and tenfold higher in the CM11 experiment, than the yield obtained using the previous protocol without culture step in conditioned medium (RPE2, 3, 5 and 6).

TABLE 2

Comparison between RPE yield in experiments CM1-4 and GMP production of HADC-RPE batches 2, 3, 5 and 6

| Experiment | Number of center well (CW) plates of hESC | Number of 6 cm dishes or flasks of hESC | Amount of pigmented RPE cells after differentiation on laminin | Amount of RPE cells at P0 on gelatin (6 well plate) | Amount of RPE cells at P0 per well | The RPE P0 yield from one hES center well plate | The average of RPE P0 yield from one hES plate |
|---|---|---|---|---|---|---|---|
| RPE2 | 30 | 15 | $6.2 \times 10^6$ | $40.5 \times 10^6$ | $5.78 \times 10^6$ | $1.3 \times 10^6$ | $1.7 \times 10^6 \pm 0.85$ |
| RPE3 | 30 | 15 | $5 \times 10^6$ | $42.3 \times 10^6$ | $7.05 \times 10^6$ | $1.4 \times 10^6$ | |
| RPE5 | 30 | 15 | $9.8 \times 10^6$ | $88.7 \times 10^6$ | $7.4 \times 10^6$ | $2.9 \times 10^6$ | |
| RPE6 | 30 | 15 | $2.5 \times 10^6$ | $30 \times 10^6$ | $6 \times 10^6$ | $1 \times 10^6$ | |
| CM1 | 4 | — | $1.1 \times 10^6$ | $12.9 \times 10^6$ | $6.45 \times 10^6$ | $3.2 \times 10^6$ | $3.6 \times 10^6 \pm 0.36$ |
| CM3 | 4 | — | $2 \times 10^6$ | $14.8 \times 10^6$ | $4.93 \times 10^6$ | $3.7 \times 10^6$ | |
| CM4 | 4 | — | $2 \times 10^6$ | $15.8 \times 10^6$ | $5.26 \times 10^6$ | $3.9 \times 10^6$ | |
| CM11 Large scale | 4 | Flask T75→T175 | $11 \times 10^6$ | $71 \times 10^6$ | $5.92 \times 10^6$ | $17.75 \times 10^6$ | NA |

Table 3 shows an extrapolated calculation of bulk production of RPE cells using the disclosed protocol.

TABLE 3

Comparison of the yield of previous and disclosed methodologies for RPE production

| | Thawing and culture in center wells plates (3w) | Expansion of hESC (3w) | Preparation of SBs and seeding on laminin (2w) | Estimated Amount of pigmented RPE cells from laminin (4w) | Estimated Amount of RPE cells at P0 (2w) | Estimated Amount of RPE cells at P1 (2w) | Estimated Amount of RPE cells in P2 (2w) |
|---|---|---|---|---|---|---|---|
| Disclosed Protocol Potential | 1→4 | 4→T75 → 8 × T175 → 32 × T175 flasks | 64 × 6 cm SBs→ 32 × 6w plates laminin | ~$320 \times 10^6$ Cultured in 16 × T175 | ~$1.6 \times 10^9$ Cultured in 80 × T175 | ~$8 \times 10^9$ Cultured in 400 × T175 | ~$40 \times 10^9$ from 400 × T175 into 3333 ampoules of $12 \times 10^6$ cells |
| Previous Protocol (No conditioned medium step) | 1→4 | 4→30→ 15 × 6 cm dishes | 3 × 6 cm SBs→ 7 × 6wells laminin | $6 \times 10^6$ seeded on 7 × 6w of gelatin | $40 \times 10^6$ Cultured in 2 × T175 | $230 \times 10^6$ Cultured in 10 × T175 | $1000 \times 10^6$ from 10 × T175 into ~666 ampoules of $1.5 \times 10^6$cells |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of production of retinal pigment epithelial (RPE) cells comprising:
   (a) culturing human pluripotent stem cells in a human feeder cell-conditioned medium in the absence of feeder cells on a non-adherent surface to obtain a cultured population of human pluripotent stem cells, wherein the feeder cell-conditioned medium is isolated from the feeder cells which are used to generate said feeder cell-conditioned medium;
   (b) differentiating said cultured population of human pluripotent stem cells in a medium comprising a differentiating agent to obtain differentiating cells, wherein the differentiating agent is selected from small molecules and proteins; and
   (c) further differentiating said differentiating cells in a medium comprising one or more members of the TGFβ superfamily, wherein a yield of between about $50\times10^6$ to about $150\times10^6$ RPE cells per 175 mL container is capable of being or can be obtained.

2. The method of claim 1, wherein the human feeder cell-conditioned medium comprises an irradiated human cord fibroblast conditioned medium.

3. The method of claim 1, wherein the differentiating agent comprises nicotinamide.

4. The method of claim 1, wherein the medium of step (b) is devoid of activin A.

5. The method of claim 1, wherein the member of the TGFβ superfamily is selected from the group consisting of TGFβ1, TGFβ3 and activin A.

6. The method of claim 1, wherein the medium of step (c) comprises nicotinamide and activin A.

7. The method of claim 1, further comprising expanding the RPE cells in a medium comprising nicotinamide and devoid of activin A following step (c).

8. The method of claim 1, wherein at least one of the culturing and differentiating steps are carried out in oxygen conditions of about 20%.

9. A method of increasing the yield of RPE cells comprising:
- (a) culturing human pluripotent stem cells in a human feeder cell-conditioned medium in the absence of feeder cells on a non-adherent surface to obtain a cultured population of human pluripotent stem cells, wherein the feeder cell-conditioned medium is isolated from the feeder cells which are used to generate said feeder cell-conditioned medium;
- (b) differentiating said cultured population of human pluripotent stem cells in a medium comprising a differentiating agent to obtain differentiating cells, wherein the differentiating agent is selected from small molecules and proteins;
- (c) further differentiating said differentiating cells in a medium comprising one or more members of the TGFβ superfamily to obtain RPE cells, wherein a yield of RPE cells obtained is increased by between about 2 to 10 fold compared to a yield of RPE cells that were not cultured in feeder cell-conditioned medium.

10. The method of claim 9, wherein the human feeder cell-conditioned medium comprises an irradiated human cord fibroblast conditioned medium.

11. The method of claim 9, wherein the differentiating agent comprises nicotinamide.

12. The method of claim 9, wherein the medium of step (b) is devoid of activin A.

13. The method of claim 9, wherein the member of the TGFβ superfamily is selected from the group consisting of TGFβ1, TGFβ3 and activin A.

14. The method of claim 9, wherein the medium of step (c) comprises nicotinamide and activin A.

15. The method of claim 9, further comprising expanding the RPE cells in a medium comprising nicotinamide and devoid of activin A following step (c).

16. The method of claim 9, wherein at least one of the culturing and differentiating steps are carried out in oxygen conditions of about 20%.

17. A method of treating a retinal disease or disorder comprising:
- (a) culturing human pluripotent stem cells in a human feeder cell-conditioned medium in the absence of feeder cells on a non-adherent surface to obtain a cultured population of human pluripotent stem cells, wherein the feeder cell-conditioned medium is isolated from the feeder cells which are used to generate said feeder cell-conditioned medium;
- (b) differentiating said cultured population of human pluripotent stem cells in a medium comprising a differentiating agent to obtain differentiating cells, wherein the differentiating agent is selected from small molecules and proteins;
- (c) further differentiating said differentiating cells in a medium comprising one or more members of the TGFβ superfamily to obtain RPE cells, wherein a yield of RPE cells obtained is increased by between about 2 to 10 fold compared to a yield of RPE cells that were not cultured in feeder cell-conditioned medium;
- (d) transplanting said RPE cells into the subject's eye, thereby treating the disease or disorder.

18. The method of claim 17, wherein the human feeder cell-conditioned medium comprises an irradiated human cord fibroblast conditioned medium.

19. The method of claim 17, wherein the differentiating agent comprises nicotinamide.

20. The method of claim 17, wherein the medium of step (b) is devoid of activin A.

21. The method of claim 17, wherein the member of the TGFβ superfamily is selected from the group consisting of TGFβ1, TGFβ3 and activin A.

22. The method of claim 17, wherein the medium of step (c) comprises nicotinamide and activin A.

23. The method of claim 17, further comprising expanding the RPE cells in a medium comprising nicotinamide and devoid of activin A following step (c).

24. The method of claim 17, wherein at least one of the culturing and differentiating steps are carried out in oxygen conditions of about 20%.

25. The method of claim 17, wherein the RPE cells are transplanted into the subretinal space of the eye.

26. The method of claim 17, wherein the RPE cells are transplanted in a suspension, as a monolayer or as multiple layers of cells immobilized on or within a matrix or a substrate.

27. The method of claim 17, wherein the retinal disease or disorder is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage due to damage caused by any one of photic, laser, inflammatory, infectious, radiation, neovascular or traumatic injury.

* * * * *